United States Patent
Katsevich

(10) Patent No.: US 7,848,479 B1
(45) Date of Patent: Dec. 7, 2010

(54) IMAGE RECONSTRUCTION FOR A GENERAL CIRCLE-PLUS TRAJECTORY

(75) Inventor: Alexander Katsevich, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 195 days.

(21) Appl. No.: 12/137,137

(22) Filed: Jun. 11, 2008

Related U.S. Application Data

(60) Provisional application No. 60/947,145, filed on Jun. 29, 2007.

(51) Int. Cl.
*A61B 6/00* (2006.01)
(52) U.S. Cl. .............................. 378/4; 378/15
(58) Field of Classification Search ............ 378/4, 378/15
See application file for complete search history.

(56) References Cited

U.S. PATENT DOCUMENTS

| | | | |
|---|---|---|---|
| 5,170,439 A | 12/1992 | Zeng et al. | |
| 5,539,800 A | 7/1996 | Katsevich et al. | |
| 5,550,892 A | 8/1996 | Katsevich et al. | |
| 5,706,325 A | 1/1998 | Hu | |
| 5,717,211 A | 2/1998 | Katsevich | |
| 5,784,481 A | 7/1998 | Hu | |
| 5,881,123 A * | 3/1999 | Tam | 378/4 |
| 6,014,419 A * | 1/2000 | Hu | 378/4 |
| 6,148,056 A | 11/2000 | Lin et al. | |
| 6,459,756 B1 * | 10/2002 | Tam et al. | 378/15 |
| 6,504,892 B1 * | 1/2003 | Ning | 378/4 |
| 6,574,299 B1 | 6/2003 | Katsevich | |
| 6,771,733 B2 | 8/2004 | Katsevich | |
| 6,804,321 B2 | 10/2004 | Katsevich | |
| 6,898,264 B2 | 5/2005 | Katsevich | |
| 6,907,100 B2 * | 6/2005 | Taguchi | 378/4 |
| 7,010,079 B2 | 3/2006 | Katsevich | |
| 7,197,105 B2 | 3/2007 | Katsevich | |
| 7,305,061 B2 | 12/2007 | Katsevich | |
| 2007/0019776 A1 * | 1/2007 | Bontus et al. | 378/4 |

* cited by examiner

*Primary Examiner*—Edward J Glick
*Assistant Examiner*—Alexander H Taningco
(74) *Attorney, Agent, or Firm*—Brian S. Steinberger; Phyllis K. Wood; Law Offices of Brian S. Steinberger, P.A.

(57) ABSTRACT

Methods, apparatus and systems for an exact filtered back projection process for circle-plus trajectories, which consist of two components: C and L. The first component C, is analogous to a circle in the traditional circle-plus trajectories, is any closed (not necessarily planar) continuous curve. The second component L is almost any continuous curve. The only condition is that L starts below C and ends above C. The process does not depend on the global properties of L. When the source is located on L, one needs to know only how C projects onto the corresponding detector and the properties of L in the immediate neighborhood of the source position. The present invention is especially convenient for the traditional circle-plus trajectories, which are implemented using a gantry and moving table by obtaining a universal FBP algorithm, which is independent of table movement during the scan as long as the condition on L is satisfied.

20 Claims, 11 Drawing Sheets

Fig. 8

Step 20. Finding families of lines for filtering.

It is assumed the x-ray source is located on $C$.

Step 21. Form a set of lines parallel to the asymptote of the projection of $C$ onto the detector that cover the projection of the region of interest inside the object being scanned. These lines are called the first half of the filtering family $L_1$.

Step 22. Form a set of lines tangent to the projection of $C$ onto the detector. These lines are called the second half of the filtering family $L_1$.

Step 23. Combine the two halves obtained in Steps 21 and 22 to form the family of filtering lines $L_1$.

Step 30

Fig. 9

Step 30. Finding families of lines for filtering.

It is assumed the x-ray source is located on $L$.

Step 31. Choose a discrete set of values of the parameter $s_t$ inside the interval $[s_t^{min}, s_t^{max}]$.

Step 32. For each $s_t$ chosen in Step 31 find a line tangent to the projection of $C$.

Step 33. From the collection of lines constructed in Step 32 retain only the lines that are tangent to the convex hull of the projection of $C$. The remaining lines form the required set of lines, which is called family $L_2$.

Step 40

Fig. 10

Step 40. Preparation for filtering

Step 41. If the x-ray source is located on $C$, fix a filtering line $l_{fl} \in L_1$.
If the x-ray source is on $L$, fix $l_{fl} \in L_2$.

↓

Step 42. Parameterize points on the said line by polar angle $\gamma$ in the plane through $y(s_0)$ and $l_{fl}$.

↓

Step 43. Choose a discrete set of equidistant values $\gamma_j$ that will be used later for discrete filtering in Step 50.

↓

Step 44. For each $\gamma_j$ find the unit vector $\beta_j$ which points from $y(s_0)$ towards the point on $l_{fl}$ that corresponds to $\gamma_j$.

↓

Step 45. Using the CB projection data $D_f(y(q),\Theta)$ for a few values of $q$ close to $s_0$ find numerically the derivative
$(\partial/\partial q)D_f(y(q),\Theta)|_{q=s_0}$ for all $\Theta = \beta_j$.

↓

Step 46. Store the computed values of the derivative in computer memory.

↓

Step 47. Repeat Steps 41-46 for all lines $l_{fl}$ identified in Steps 20 and 30. This way we will create the processed CB data $\Psi(s_0, \beta_j)$

↓

Step 50

Fig. 11

Step 50. Filtering

Step 51. Fix a filtering line $l_{ft}$. If the x-ray source is located on the $C$, take $l_{ft} \in L_1$. If the x-ray source is located on the $L$, take $l_{ft} \in L_2$.

↓

Step 52. Compute FFT of the values of the said processed CB data computed in Step 40 along the said line.

↓

Step 53. Compute FFT of the filter $1/\sin\gamma$

↓

Step 54. Multiply FFT of the filter $1/\sin\gamma$ (the result of Step 53) and FFT of the values of the said processed CB data (the result of Step 52).

↓

Step 55. Take the inverse FFT of the result of Step 54.

↓

Step 56. Store the result of Step 55 in computer memory.

↓

Step 57. Repeat Steps 51-56 for all lines in the said family of lines. This will give the filtered CB data $\Phi(s_0, \beta_j)$.

↓

Step 60

Fig. 12    Step 60. Back-projection

Step 61. Fix a reconstruction point $x$, which represents a point inside the patient where it is required to reconstruct the image.

Step 62. If $s_0 \in I_C \cup I_L(x)$, then the said filtered CB data affects the image at $x$ and one performs Steps 63-68. If $s_0 \notin I_C \cup I_L(x)$, then the said filtered CB data is not used for image reconstruction at $x$. In this case go back to Step 61 and choose another reconstruction point.

Step 63. Find the projection $\hat{x}$ of $x$ onto the detector plane $DP(s_0)$ and the unit vector $\beta(s_0,x)$, which points from $y(s_0)$ towards $x$.

Step 64. Identify filtering lines $l_{\mu} \in L_1$ or $l_{\mu} \in L_2$ (depending on where the x-ray source is located) and points on the said lines that are close to $\hat{x}$. This will give values of $\Phi_m(s_0,\beta_j), m \geq 1$ for $\beta_j$ close to $\beta(s_0,x)$.

Step 65. With interpolation estimate the value of $\Phi_m(s_0,\beta(s_0,x))$ from the said values of $\Phi_m(s_0,\beta_j)$ for $\beta_j$ close to $\beta(s_0,x)$.

Step 66. Compute the contribution from the said filtered CB data to the image being reconstructed at $x$ by multiplying $\Phi_m(s_0,\beta(s_0,x))$ by $-c_m(s_0,x)/(4\pi^2 |x-y(s_0)|)$ (see Eq. 6 for definition of $c_m(s_0,x)$).

Step 67. Add the said contribution to the image being reconstructed at the point $x$ according to a pre-selected scheme for approximate evaluation of the integral in equation 14.

Step 68. Go to Step 61 and choose a different reconstruction point $x$.

IMAGE RECONSTRUCTION FOR A GENERAL CIRCLE-PLUS TRAJECTORY

This application claims the benefit of priority to U.S. Provisional Application No. 60/947,145 filed on Jun. 29, 2007 and was funded in part by NSF grant DMS-0505494.

FIELD OF THE INVENTION

This invention relates to image reconstruction and, in particular, to methods and systems for reconstructing three dimensional images from the data obtained by a general circle-plus scan of an object, such as when the C-arm rotates around an object along a first curve C, and then the C-arm moves along the object along the curve L, and C is a piece-wise smooth closed curve, not necessarily a circle, and L is an additional piece-wise smooth curve with the condition that L starts below C or on C and ends above C.

BACKGROUND AND PRIOR ART

Over the last thirty years, computer tomography (CT) has gone from image reconstruction based on scanning in a slice-by-slice process to spiral scanning to also include non-spiral scanning techniques such as those performed with C-arm devices, with all techniques and devices experiencing problems with image reconstruction.

From the 1970s to 1980s the slice-by-slice scanning was used. In this mode the incremental motions of the patient on the table through the gantry and the gantry rotations were performed one after another. Since the patient was stationary during the gantry rotations, the trajectory of the x-ray source around the patient was circular. Pre-selected slices through the patient were reconstructed using the data obtained by such circular scans.

From the mid 1980s to present day, spiral type scanning has become the preferred process for data collection in CT. Under spiral scanning a table with the patient continuously moves at a constant speed through the gantry that is continuously rotating about the table. At first, spiral scanning has used one-dimensional detectors, which receive data in one dimension (a single row of detectors). Later, two-dimensional detectors, where multiple rows (two or more rows) of detectors sit next to one another, have been introduced. In CT there have been significant problems for image reconstruction especially for two-dimensional detectors. Data provided by the two-dimensional detectors will be referred to as cone-beam (CB) data or CB projections.

In addition to spiral scans there are non-spiral scans, in which the trajectory of the x-ray source is different from spiral. In medical imaging, non-spiral scans are frequently performed using a C-arm device, which is usually smaller and more portable than spiral type scanning systems. For example, C-arm scanning devices have been useful for being moved in and out of operating rooms, and the like.

FIG. 1 shows a typical prior art arrangement of a patient on a table that moves through a C-arm device, that is capable of rotating around the patient, having an x-ray tube source and a detector array, where cone beam projection data sets are received by the x-ray detector, and an image reconstruction process takes place in a computer with a display for the reconstructed image.

There are known problems with using C-arm devices to reconstruct images. See in particular for example, pages 755-759 of Kudo, Hiroyuki et al., Fast and Stable Cone-Beam Filtered Back projection Method for Non-planar Orbits, IOP Publishing LTD, 1998, pp. 747-760. The Kudo paper describes image reconstruction using C-arm devices for various shift-variant filtered back projection (FBP) structures, which are less efficient than convolution-based FBP algorithms.

For three-dimensional, also known as volumetric, image reconstruction from the data provided by spiral and non-spiral scans with two-dimensional detectors, there are two known groups of algorithms: Exact algorithms and Approximate algorithms, that each have known problems. Under ideal circumstances, exact algorithms can provide a replication of an exact image. Thus, one should expect that exact algorithms would produce images of good quality even under non-ideal (that is, realistic) circumstances.

However, exact algorithms can be known to take many hours to provide an image reconstruction, and can take up great amounts of computer power when being used. These algorithms can require keeping considerable amounts of cone beam projections in memory. Some other exact algorithms are efficient, but may require excessive amounts of CB data, which results in an increased x-ray dose to the patient.

Approximate algorithms possess a filtered back projection (FBP) structure, so they can produce an image very efficiently and using less computing power than Exact algorithms. However, even under the ideal circumstances these algorithms produce an approximate image that may be similar to but still different from the exact image. In particular, approximate algorithms can create artifacts, which are false features in an image. Under certain circumstances and conditions these artifacts could be quite severe.

To date, there are no known algorithms that can combine the beneficial attributes of exact and approximate algorithms into a single algorithm that is capable of replicating an exact image under the ideal circumstances, uses small amount of computer power, requires minimal amount of CB data, and reconstructs the exact images in an efficient manner (i.e., using the FBP structure) in the cases of general circle-plus trajectories.

Hereinafter the phrase that "the process of the present invention reconstructs an exact image" means that the process is capable of reconstructing an exact image. Since in real life any data contains noise and other imperfections, no algorithm is capable of reconstructing an exact image.

Image reconstruction has been proposed in many U.S. Patents. See for example, U.S. Pat. Nos. 5,663,995 and 5,706,325 and 5,784,481 and 6,014,419 to Hu; 5,881,123 and 5,926,521 and 6,130,930 and 6,233,303 and 6,292,525 to Tam; 5,960,055 to Samaresekera et al.; 5,995,580 to Schaller; 6,009,142 to Sauer; 6,072,851 to Sivers; 6,173,032 to Besson; 6,198,789 to Dafni; 6,215,841 and 6,266,388 to Hsieh. Other U.S. patents have also been proposed for image reconstruction as well. See U.S. Pat. Nos. 6,504,892 to Ning; 6,148,056 to Lin; 5,784,481 to Hu; 5,706,325 to Hu; and 5,170,439 to Zeng et al.

Mathematically, the problem of image reconstruction in computer tomography (CT) consists of finding an unknown function $f(x)$, $x \in P^3$, from its integrals along lines that intersect a curve. The curve is called the source trajectory, and the collection of line integrals is called the cone beam data. A typical CT scanner consists of two major parts: a gantry and patient table. The gantry is a doughnut-shaped device, where an x-ray source and x-ray detector are located opposite each other. The patient lies on the table, which is then inserted into the rotating gantry. By transmitting x-rays through the patient the cone beam data are collected. By varying the motion of the table through the gantry one obtains different source trajectories. To simplify mathematics, one usually assumes that the patient is stationary, and the gantry moves relative to the patient.

Cardiac and, more generally, dynamic imaging is a very important challenge for modern tomography. Circle is usually the most convenient trajectory. As opposed to helix, in a circular scan the gantry does not move away from the dynamically changing region of interest. As opposed to the helix, in the circular scan the gantry does not move away from the dynamically changing region of interest (ROI). As opposed to a saddle trajectory, the circular scan does not involve moving the patient back and forth, which can be uncomfortable. The major disadvantage of the circular trajectory is its incompleteness. For this reason a pure circular scan is complemented by an additional trajectory, such as a line, arc, helical segment, etc., which makes it complete. So the problem of developing a reconstruction algorithm for such trajectories is of significant practical interest.

Theoretically exact and efficient filtered back projection (FBP) algorithms have been developed for a number of specific circle-plus trajectories, such as circle+line described in Image reconstruction for the circle and line trajectory, Physics in Medicine and Biology, 2004, pp. 5059-5072, vol. 49, circle+arc described in Image reconstruction for the circle and arc trajectory, Physics in Medicine and Biology, 2005, pp. 2249-2265, vol. 50; G. H. Chen, T. L. Zhuang, S. Leng, and B. E. Nett, Shift-invariant and mathematically exact cone-beam FBP reconstruction using a factorized weighting function, IEEE Transactions on Medical Imaging, 2006, circle+helical segment described in C. Bontus, P. Koken, Th. Köhler, R. Proksa, Circular CT in combination with a helical segment, Physics in Medicine and Biology, 2007, pp. 107-120, vol. 51.

A very nice exact FBP algorithm was recently proposed by J. D. Pack, F. Noo. R. Clackdoyle, Cone-beam reconstruction using the back-projection of locally filtered projections, IEEE Transactions on Medical Imaging, 2005, pp. 1-16, vol. 24. It applies to almost any source trajectory, but sometimes leads to excessive detector requirements. The problem is that the algorithm is too general and does not take the geometry of the curve into account.

Back projection-filtration (BPF) algorithms are very flexible and can be easily derived for almost any scanning curve described in T. Zhuang, S. Leng, B. E. Nett, G. Chen, Fan-beam and cone-beam image reconstruction via filtering the backprojection image of differentiated projection data, Physics in Medicine and Biology, 2004, pp. 1643-1657, vol. 49; J. D. Pack, F. Noo, Cone-beam reconstruction using 1D filtering along the projection of M-lines, Inverse Problems, 2005, pp. 1105-1120, vol. 21; J. D. Pack, F. Noo, R. Clackdoyle, Cone-beam reconstruction using the back-projection of locally filtered projections, IEEE Transactions on Medical Imaging, 2005, pp. 1-16, vol. 24; Y. Zou, X. Pan, D. Xia, G. Wang, PI-line-based image reconstruction in helical cone-beam computed tomography with a variable pitch, Medical Physics, 2005, pp. 2639-2648, vol. 32; E. Y. Sidky, Y. Zou, X. Pan, Minimum data image reconstruction algorithms with shift-invariant filtering for helical, cone-beam CT, Physics in Medicine and Biology, 2000, pp. 91-100, vol. 11; H. Yu, S. Zhao, Y. Ye, G. Wang, Exact BPF and FBP algorithms for nonstandard saddle curves, Medical Physics, 2005, pp. 3305-3312, vol. 32; Y. Ye. S. Zhao, H. Yu, G. Wang, A general exact reconstruction for cone-beam CT via backprojection-filtration, IEEE Transactions on Medical Imaging, 2005, pp. 1190-1198, vol. 24; T. Zhuang, G. H. Chen, New families of exact fan-beam and cone-beam image reconstruction formulae via filtering the back projection image of differentiated projection data along singly measured lines, Inverse Problems, 2006, pp. 991-1006, vol. 22, but they are generally less efficient than their FBP counterparts.

The problem to be solved is the development of a reconstruction algorithm for such trajectories, such as circle+line, circle+arc, circle+helical segments and almost any continuous curve C plus an additional curve L under the condition that L starts below or on C and ends above C. Back projection-filtration algorithms are very flexible and can be easily derived for almost any scanning curve, but they are generally less efficient than their filtered back projection counterparts.

What is needed is a reconstruction algorithm for almost any continuous curve C plus an additional curve L under the condition that L starts below or on C and ends above C implemented using shift-invariant filtered back projection with only a few one-dimensional families of filtering lines.

SUMMARY OF THE INVENTION

A primary objective of the invention is to provide methods, apparatus and systems for an exact filtered back projection process for a general class of circle-plus trajectories, which consist of two components: C and L where C is analogous to a circle in a traditional circle-plus trajectory and L which is almost any continuous curve under the condition that L starts below or on C and ends above C.

A secondary objective of the invention is to provide methods, apparatus and systems for image reconstruction for a general circle-plus trajectory that does not depend on the global properties of L.

A third objective of the invention is to provide methods, apparatus and systems for image reconstruction for a general circle-plus trajectory that is completely independent of how the table moves during the scan as long as L starts below or on C and ends above C.

A fourth objective of the invention is to provide methods, apparatus and systems for image reconstruction for a general circle-plus trajectory including trajectories such as circle+line, circle+arc, circle+helical segments and almost any continuous curve C plus another curve L under the condition that L starts below or on C and ends above C.

A fifth objective of the invention is to provide methods, apparatus and systems for image reconstruction for a general circle-plus trajectory where the class of curves encompasses practically all prior art circle-plus trajectories and includes many more new ones, such as various saddle-plus trajectories.

Methods, systems and apparatus for an exact filtered back projection process for circle-plus trajectories, which consist of two components: C and L. The first component C, is analogous to a circle in the traditional circle-plus trajectories, is essentially any closed (e.g., not necessarily planar) continuous curve. The second component L is almost any continuous curve. The only condition is that L starts below or on C and ends above C. The process does not depend on the global properties of L. When the source is located on L, one needs to know only how C projects onto the corresponding detector and the properties of L in the immediate neighborhood of the source position. The present invention is especially convenient for the traditional circle-plus trajectories, which are implemented using a gantry and moving table by obtaining a universal FBP algorithm, which is independent of how the table moves during the scan as long as the condition on L is satisfied.

A first embodiment provides a method for reconstructing an exact or quasi-exact image from cone beam data provided by at least one detector for a general circle-plus trajectory. The method includes (a) scanning an object using an x-ray source, (b) collecting cone beam data of the object, wherein the cone beam data corresponds to a general circle-plus trajectory relative to the object; the general circle-plus trajectory including a C component and an L component, wherein C is any closed curve, and L is an additional curve that guarantees completeness of the cone beam data for at least one reconstruction point, (c) reconstructing an exact or quasi-exact image of the scanned object from the circle-plus trajectory cone beam data using a convolution based Filtered Back Projection algorithm, wherein for each point on L the step of reconstructing does not depend on the global properties of L. The component L can be a constant pitch helix, a variable pitch helix or other trajectory that meets the condition. The C component is a circle and component L lies on a surface of a cylinder with base C as the component C.

Reconstructing the image includes shift invariant filtering of the cone beam data and back projection updating the exact or quasi-exact image of the scanned object. For each source position on the component L in shift invariant filtering is independent of global properties of L, and a direction of filtering is determined by how the component C projects on the detector. For each source position on the component L the step of back projection updating is independent of the global properties of L and for each source position on the component L filtering is performed along curves tangent to a convex hull of the projection of component C on the detector.

A second embodiment provides a method for reconstructing an image from cone beam data provided by at least one detector for a general circle-plus trajectory. The method includes scanning an object using an x-ray source, collecting cone beam data of the object, wherein the cone beam data corresponds to a general circle-plus trajectory relative to the object; the general circle-plus trajectory including a C component and an L component, wherein C is any closed curve, and L is an additional curve and identifying lines on a plane Π intersecting the cone beam. The identification includes when the x-ray source belongs to the component C, project C onto Π and select a discrete set of lines tangent to that projection or parallel to an asymptote of the projection, when the x-ray source belongs to the component L, project C onto Π and select a discrete set of lines tangent to a convex hull of that projection. The image reconstruction method also includes preprocessing and shift invariant filtering said data along said lines, back projecting said filtered data to form a precursor of said image, and repeating steps until the image of the object is reconstructed.

In the second embodiment, the preprocessing includes computing a derivative $(\partial/\partial s)D_f(y(s),\Theta)$, wherein s is a parameter along a scan path, which determines point y(s) on the path, $D_f(y,\Theta)$ is a cone beam transform of $f$ corresponding to the x-ray source located at a point y and a direction $\Theta$, and $f$ is a function describing the object being scanned. The back projection step includes fixing a reconstruction point x which represents a point inside the object being scanned to reconstruct the image, (eii) fixing a source position y(s) on L and locating a projection $\hat{x}$ of x onto the detector which corresponds to the source located at y(s), when $\hat{x}$ is projected inside a convex hull of the projection of component C on the detector, the cone beam data corresponding to source position y(s) is not used for image reconstruction at x, and when $\hat{x}$ is projected outside the convex hull of the projection of C on the detector, the cone beam data corresponding to source position y(s) is used for image reconstruction at x.

A third embodiment provides A method for reconstructing an exact or quasi-exact image from cone beam data provided by at least one detector for a circle-plus trajectory. The method includes scanning an object using an x-ray source, collecting cone beam data of the object, wherein the cone beam data corresponds to a circle-plus trajectory relative to the object, the circle-plus trajectory including a C component and an L component, wherein component C is a circle, and component L is an additional curve which lies on the surface of a right circular cylinder with base C, and reconstructing an exact or quasi-exact image of the scanned object from the circle-plus trajectory cone beam data using a convolution based Filtered Back Projection algorithm, wherein for each source position on component L, the source being physical or virtual, the step of reconstructing depends only on a distance between a current source position and a plane of component C and on the properties of component L in a neighborhood of the current source position. In this embodiment, component L can be a constant pitch helix or a variable pitch helix. The step of reconstructing includes shift invariant filtering of the cone beam data projections, and back projection updating the image of the scanned object. For each source position on the component L filtering is performed along curves tangent to the projection of component C on the detector.

Further objects and advantages of this invention will be apparent from the following detailed description of preferred embodiments which are illustrated schematically in the accompanying drawings.

BRIEF DESCRIPTION OF THE FIGURES

FIG. 8 is a three substep flow chart for identifying the set of lines, which corresponds to step 20 of FIG. 2.

FIG. 9 is a three substep flow chart for identifying the set of lines, which corresponds to step 30 of FIG. 2.

FIG. 10 is a seven substep flow chart for preparation for filtering, which corresponds to step 40 of FIG. 2.

FIG. 11 is a seven substep flow chart for filtering, which corresponds to step 50 of FIG. 2.

FIG. 12 is an eight substep flow chart for back projection, which corresponds to step 60 of FIG. 2.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

U.S. Pat. No. 7,305,016, U.S. Pat. No. 7,010,079, U.S. Pat. No. 6,804,321, U.S. Pat. No. 6,771,733, U.S. Pat. No. 6,574,299 all having a common inventor and assigned to the same assignee are incorporated herein by reference.

Figure 1:
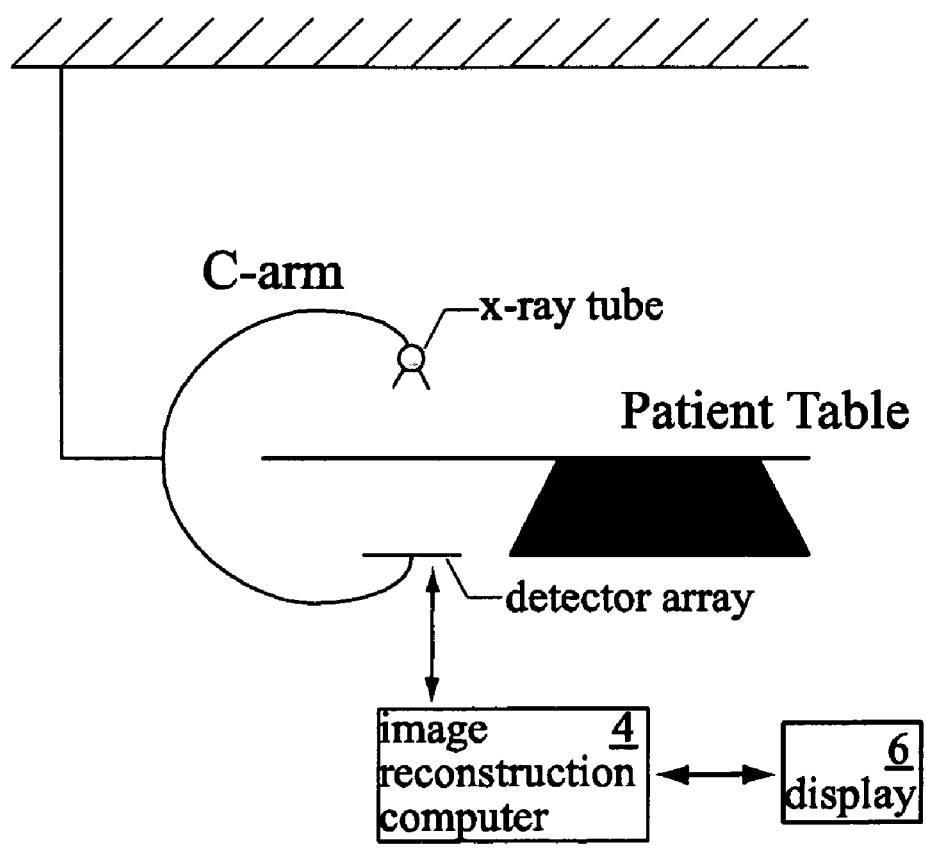
FIG. 1 shows a typical prior art view arrangement of a patient on a table that moves through a C-arm device and an image reconstruction process takes place in a computer with a display for the reconstructed image.

As previously described, FIG. 1 shows a typical prior art view arrangement of a patient on a table that moves through an C-arm device such as the AXIOM Artis MP, manufactured by Siemens, that is capable of rotating around the patient, having an x-ray tube source and a detector array, where cone beam projections are received by the x-ray detector, and an image reconstruction process takes place in a computer 4 with a display 6 for displaying the reconstructed image. For the subject invention, the detector array can be a two-dimensional detector array. For example, the array can include two, three or more rows of plural detectors in each row. When three rows are used with each row having ten detectors, then one CB projection set would be thirty individual x-ray detections.

Alternatively, a conventional gantry, such as ones manufactured by Siemens, Toshiba, General Electric, and the like, can be used, as shown by the dotted concentric lines, for the X-ray sources and detector array. The gantry can rotate partially, and up to a full circle, or greater than a full circle.

The present invention provides methods, systems and apparatus for an exact filtered back projection process for a general class of circle-plus trajectories, which consist of two components: C and L. The first component C, which is analogous to a circle in the traditional circle-plus trajectories, is essentially any closed (e.g., not necessarily planar) continuous curve. The second component L is almost any continuous curve. The only condition is that L starts below C and ends above C. The distinctive feature of the present invention is that it does not depend on the global properties of L. When the source is located on L, it is necessary to know only how C projects onto the corresponding detector and the properties of L in the immediate neighborhood of the source position.

The present invention is especially convenient for the traditional circle-plus trajectories, which are implemented using a gantry and moving table. In this case we obtain a universal FBP algorithm, which is completely independent of how the table moves during the scan provided that the main condition on L is satisfied. The results of testing the algorithm on two circle+helix trajectories demonstrate good image quality.

The class of curves encompasses practically all prior art circle-plus trajectories and includes many more new ones, such as various saddle-plus trajectories, etc. The distinctive feature of the present invention is that it does not depend on the global properties of L. When the source is located on L, the only thing one needs to know is how C projects onto the corresponding detector. The algorithm is especially convenient for the traditional circle-plus trajectories, which are implemented using a gantry and moving table. Here C is a circle, and L lies on the surface of the cylinder with base C. Regardless of how the table moves during the scan, the projection of C onto the detector only depends on the axial distance between $y(s) \in L$ and the plane of the circle.

Consequently, a universal FBP process is provided, which is completely independent of the shape of L as long as the main condition is satisfied. This implies that the circle+line algorithm of the paper by A. Katsevich, Image reconstruction for the circle and line trajectory, Physics in Medicine and Biology, 49 (2004), pp. 5059-5072, is a particular case of the new process and that it works for other trajectories, e.g. circle+helix, circle+variable pitch helix, etc., without modifications.

Let C be a piece-wise smooth closed curve, and L—an additional piece-wise smooth curve, which is not closed. Given $x \notin C \cup L$, let $\Xi_C(x)$ denote the set of planes through x which do not intersect C. Define $U_0$ as the set of all x such that
1. $\Xi_C(x) \neq \emptyset$, and
2. for almost all $\Pi \in \Xi_C(x)$ the number of intersection points (IPs) in $\Pi \cap L$ is odd.

The main assumption about C and L is that $U_0$ contains an open set. The first condition above is not restrictive. If $\Xi_C(x)$ is empty, then any plane through x intersects C, and L is not required for image reconstruction at x.

Next the meaning of the second condition is discussed. For $x \in U_0$ define two cones with vertex at x (see FIG. 3):

$$K_C^+(x):=\{z \in P^3: z=x+\lambda_1(y_1-x)+\lambda_2(y_2-x), y_1, y_2 \in C, \lambda_1 \lambda_2 > 0\},$$

$$K_C^-(x):=\{z \in P^3: z=x+\lambda_1(y_1-x)+\lambda_2(y_2-x), y_1, y_2 \in C, \lambda_1 \lambda_2 < 0\}. \quad (1)$$

For convenience, the point x is not included in the cones. Select $\Pi \in \Xi_C(x)$, i.e. $\Pi \cap C = \emptyset$. Since C is a continuous curve, C stays on one side of $\Pi$. Using that $K_C^-(x)-x=-(K_C^+(x)-x)$, it is concluded that $K_C^-(x)$ and $K_C^+(x)$ are located on the opposite sides of $\Pi$. In particular, the cones do not intersect.

Let $y_f$ and $y_1$ be the first and last endpoints of L, respectively. The order of endpoints is determined according to the parametrization of L. We establish the following result.

An open set $U \subset U_0$ is selected. Then for any $x \in U$ only two cases are possible:

$$y_f \in K_C^+(x), y_1 \in K_C^-(x) \text{ or } y_f \in K_C^-(x), y_1 \in K_C^+(x). \quad (2)$$

Proof Fix some $x \in U$ and consider all possible alternatives to equation 2.

Case 1: both $y_f$ and $y_1$ belong to the same cone, i.e. either $y_f, y_1 \in K_C^-(x)$ or $y_f, y_1 \in K_C^+(x)$. Select any plane $\Pi \in \Xi_C(x)$. As previously discussed, $\Pi$ does not intersect the cones. So $y_f$ and $y_1$ are on the same side of $\Pi$, and $\Pi \cap L$ contains an even number of IPs. This contradicts the assumption that the number of IPs is odd, so case 1 does not happen.

Case 2: either $y_f$ or $y_1$ is outside both cones. Suppose, for example, that $y_f \notin K_C^-(x) \cup K_C^+(x)$. Let $\Lambda$ be the union of the line through $y_f$ and $y_1$ and all the lines tangent to L. Assume at the beginning that $x \notin \Lambda$. It is clear from equation 1 that the cones $K_C^\pm(x)$ are convex. Therefore we can find $\Pi \in \Xi_C(x)$, which passes through $y_f$, does not contain $y_1$, intersects L transversely, and the tangent vector to L at $y_f$ is transversal to $\Pi$. Thus the number of Ips in $\Pi' \cap L$ is finite for all $\Pi' \in \Xi_C(x)$ sufficiently close to $\Pi$. Suppose there are N Ips in $\Pi \cap L$. Since $y_f$ is an end-point of L and $y_1 \notin \Pi$, we can find an open set of planes in a neighborhood of $\Pi$, which have N Ips with L, and another open set of planes in a neighborhood of $\Pi$, which have N−1 Ips with L. Since either N or N−1 is even, this is again a contradiction.

The argument shows that equation 2 applies to almost all $x \in U$. By continuity, equation 2 applies to all $x \in U$.

In what follows, assume that an open set $U \subset U_0$ is fixed. Define:

$$U_+ := \{x \in U: y_f \in K_C^+(x), y_1 \in K_C^-(x)\},$$

$$U_- := \{x \in U: y_f \in K_C^-(x), y_1 \in K_C^+(x)\}. \quad (3)$$

The argument implies that $U = U_- \cup U_+$.

Figure 3:
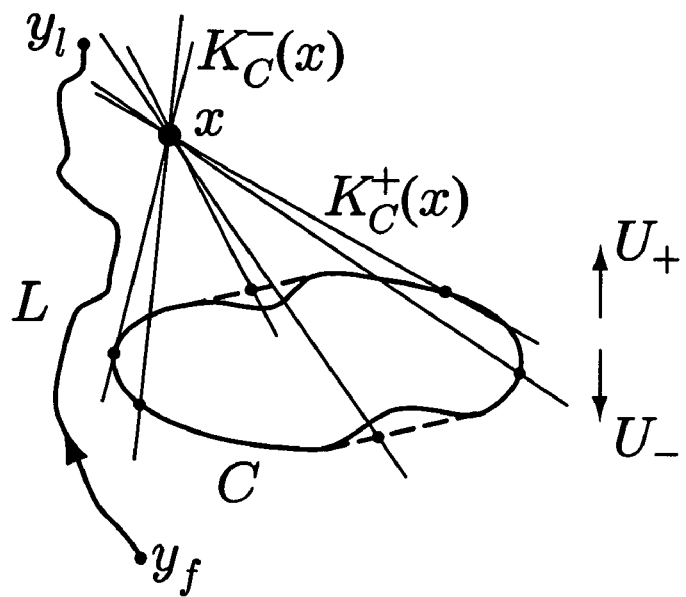
FIG. 3 shows the cones $K_C^{\pm}(x)$.

If the direction from $y_f$ to $y_1$ is called "upward", then we say that the points in $U_-$ are below C, while the points in $U_+$ are above C as shown in FIG. 3. For the classical circle+line trajectory this definition gives the usual notions of "above the circle" and "below the circle". Summarizing, condition (2) above ensures that the endpoints of L be on opposite sides of C.

Following the general scheme described in A. Katsevich, A general scheme for constructing inversion algorithms for cone beam CT, International Journal of Mathematics and Mathematical Sciences, 21 (2003), pp. 1305-1321, a normalized weight function is defined. Let $n_c(\Pi)$ denote the number of IPs in $\Pi \cap C$, where $\Pi$ is a plane through $x \in U$.

(1) If $n_c(\Pi)>0$, each IP in $\Pi \cap C$ gets weight $1/n_c$, and each IP in $\Pi \cap L$ (if they exist) gets weight zero.

(2) If $n_c(\Pi)=0$, then the IPs in $\Pi \cap L$ get weights +1, −1, +1, −1, . . . , +1, respectively.

It is assumed that if $\Pi$ does not intersect C, then the number of IPs in $\Pi \cap L$ is odd. The second rule above can be formulated as follows: odd-indexed IPs in $\Pi \cap L$ get weight +1, and even-indexed IPs in $\Pi \cap L$ get weight −1.

The main difference between the present invention and the one in C. Bontus, P. Koken, Th. Köhler, and R. Proksa, Circular CT in combination with a helical segment, Physics in Medicine and Biology, volume 51 (2007), pages 107-120, is the definition of the weight function in the case $n_c(\Pi)=0$, i.e. when all the IPs are on L. In Bontus, the IP closest to C gets a weight of 1, while all other IPs get a weight of zero. It turns out that by assigning alternating weights +1 and −1 to the IPs on L a much more flexible and simple algorithm is achieved, in which there is no need to filter along directions tangent to L.

To develop the corresponding reconstruction algorithm some parameterizations of C and L are set:

$$P \ni I_C \to y(s) \in C, P \ni I_L \to y(s) \in L, \quad (4)$$

where s is a parameter along a curve (C or L);

y(s) is the source position (or, focal point) on the corresponding curve; and $I_C$ and $I_L$ are the parametric intervals used to describe the corresponding curve.

According to A. Katsevich, A general scheme for constructing inversion algorithms for cone beam CT, International Journal of Mathematics and Mathematical Science, 21 (2003), pp. 1305-1321, which is incorporated herein by reference hereto, denote $$\phi(s,x,\theta) := sgn(\alpha \cdot \dot{y}(s)) n(s,x,\alpha), \alpha = \alpha(\theta) \in \beta^\perp(s,x) \quad (5)$$

where $x \in U$ is a reconstruction point, $\beta(s,x) := (x-y(s))/|x-y(s)|$ is the unit vector from the focal point y(s) pointing towards the reconstruction point x, $\theta$ is a polar angle in the plane perpendicular to $\beta(s,x)$, n(x, x, a) is the weight assigned to the IP $y(s) \in (C \cup L) \cap (x, \alpha)$, $\Pi(x,\alpha)$ is the plane through x and perpendicular to $\alpha$, $\alpha$ is a unit vector perpendicular to $\beta(s,x)$, which depends on the polar angle $\theta$, $\dot{y}(s)$ is the derivative of the vector function y(s) with respect to s.

By construction, $n(s,x,\alpha)$ is piecewise constant. Hence $\phi(s, x, \theta)$ is piecewise constant as well. For a fixed $x \in U$ and $s \in I := I_C \cup I_L$ let $\theta_m := \theta_m(s,x) \in [0,\pi)$ be the points where $\phi(s,x, \theta)$ is discontinuous, and $c_m(s,x)$ be values of the jumps:

$$c_m(s, x) := \lim_{\varepsilon \to 0^+} (\phi(s, x, \theta_m + \varepsilon) - \phi(s, x, \theta_m - \varepsilon)). \quad (6)$$

The general inversion formula is as follows:

$$f(x) = -\frac{1}{4\pi^2} \int_I \sum_m \frac{c_m(s, x)}{|x - y(s)|} \times \int_0^{2\pi} \frac{\partial}{\partial q} D_f(y(q), \cos\gamma\beta(s, x) + \quad (7)$$

$$\sin\gamma\alpha^\perp(s, x, \theta_m)) \bigg|_{q=s} \frac{d\gamma}{\sin\gamma} ds\alpha^\perp(s, x, \theta) :=$$

$$\alpha'(\theta) = \beta(s, x) \times \alpha(\theta), x \in U,$$

where $D_f(y,\Theta)$ is the cone beam transform of $f \in C_0^\infty(P^3 \setminus (C \cup L))$:

$$D_f(y, \Theta) = \int_0^\infty f(y + t\Theta) dt, \Theta \in S^2, \quad (8)$$

$S^2$ is the unit sphere in $P^3$.

From equations 6, 7, the filtering planes (and, therefore, filtering lines on a detector) are determined by finding the discontinuities of $\phi(s,x,\theta)$. Let a reconstruction point $x \in U$ be fixed. Consider two cases: $y(s) \in C$ and $y(s) \in L$.

(I) $y(s) \in C$. Using exactly the same argument as in Section 3 of A. Katsevich, A general scheme for constructing inversion algorithms for cone beam CT, International Journal of Mathematics and Mathematical Science, 21 (2003), pp. 1305-1321, it is found that there are two families of filtering planes. One family consists of planes through y(s), which are parallel to $\dot{y}(s)$. The second family consists of planes through y(s), which are tangent to C at other points y(q), $q \in I_C$. The values of the jump $c_m(s,x)$ can be easily computed for each specific trajectory C.

(II) $y(s) \in L$. It can be assumed that there exists a plane $\Pi \in \Xi_C(x)$ through y(s). Otherwise $\phi(s,x,\theta) \equiv 0$, and this value of s is not used in the integral in equation 7. Let $\Pi_{s,x}(\theta)$ denote the plane through y(s), x and perpendicular to $\alpha(\theta)$ (cf. equation 5). Clearly, only the following three subcases need to be considered.

(IIa) $\Pi_{s,x}(\theta_0)$ is tangent to L at some y(q), $q \neq s$. As $\theta$ passes through $\theta_0$, two more IPs in $\Pi_{s,x}(\theta) \cap L$ appear (or, disappear) in a neighborhood of y(q). Since $y(s) \neq y(q)$, the index of the IP y(s) retains its parity (even or odd) before and after the intersection. Hence $\phi(s,x,\theta)$ is continuous across $\theta_0$.

(IIb) $\Pi_{s,x}(\theta_0)$ is tangent to L at y(s). As $\theta$ passes through $\theta_0$, y(s) changes places with another neighboring IP. This results in the change of parity of y(s). Hence $n(s,x,\alpha(\theta))$ changes sign. At the same time $sgn(\alpha(\theta) \cdot \dot{y}(s))$ changes sign as well, so $\phi(s,x,\theta)$ is continuous across $\theta_0$.

Figure 4:
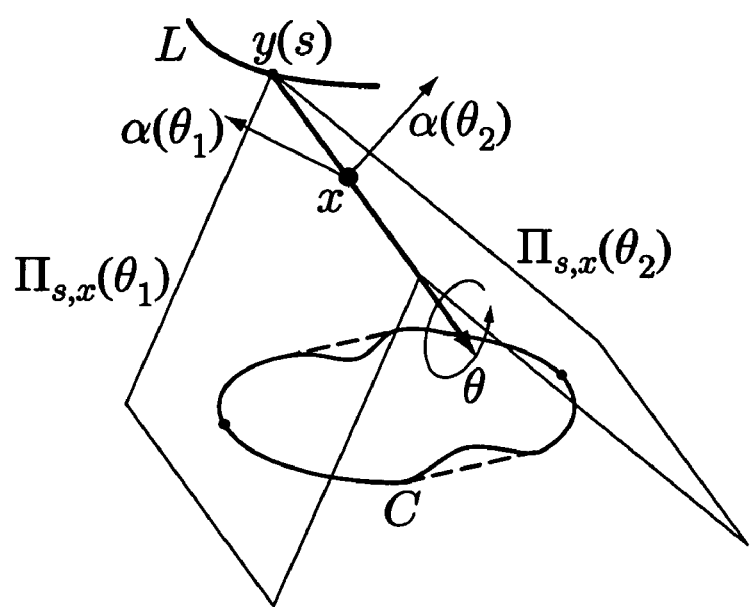
FIG. 4 shows planes tangent to C for the first and the last time.

(IIc) $\Pi_{s,x}(\theta_0)$ is tangent to C for the first (or, last) time (see FIG. 4). It is said that $\Pi_{s,x}(\theta_0)$ is tangent to C for the first time if $\Pi_{s,x}(\theta_0^-) \cap C = \emptyset$ and $\Pi_{s,x}(\theta_0^+) \cap C \neq \emptyset$. Similarly, $\Pi_{s,x}(\theta_0)$ is tangent to C the last time if $\Pi_{s,x}(\theta_0^+) \cap C \neq \emptyset$ and $\Pi_{s,x}(\theta_0^-) \cap C = \emptyset$. It turns out that in both cases $\phi(s,x,\theta)$ is discontinuous across $\theta_0$. To find the value of the jump we need to know whether y(s) is an even or odd IP. By making two observations: (a) C lies on one side of the plane $\Pi_{s,x}(\theta_0)$ (i.e., C lies in one of the half-spaces determined by $\Pi_{s,x}(\theta_0)$), and (b) the curve L is traced out from $y_f$ to $y_1$ (cf. the paragraph preceeding equation 2), it is seen that the following rule holds:

R1. $x \in U_+$. When $\dot{y}(s)$ points from the side of $\Pi_{s,x}(\theta_0)$, where C is located, towards the other side, then y(s) is an odd IP. Otherwise y(s) is an even IP.

R2. $x \in U_-$. When $\dot{y}(s)$ points from the side of $\Pi_{s,x}(\theta_0)$, where C is located the other side, then y(s) is an even IP. Otherwise y(s) is an odd IP.

Next, the values of the jumps are determined. For consistency, the same convention as in the circle+line case is used as described in A. Katsevich, Image reconstruction for the circle and line trajectory, Physics in Medicine and Biology, 49 (2004), pp. 5059-5072, which gives the direction of filtering from left to right:

C1. $\theta$ rotates in the clockwise direction (as seen from y(s)).
C2. If $x \in U_+$, $\alpha(\theta_0)$ points from the side of $\Pi_{s,x}(\theta_0)$ where C is located towards the other side.
C3. If $x \in U_-$, $\alpha(\theta_0)$ points from the side of $\Pi_{s,x}(\theta_0)$ where there is no C towards the side where C is located.

Suppose $\Pi_{s,x}(\theta_1)$ is tangent to C for the first time, and $\Pi_{s,x}(\theta_2)$ is tangent to C for the last time as shown in FIG. 4. Thus, $$n(s,x,\alpha(\theta_1^+))=n(s,x,\alpha(\theta_2^-))=0. \tag{9}$$

To determine $n(s,x,\alpha(\theta_1^-))$ and $n(s,x,\alpha(\theta_2^+))$ it is necessary to know whether y(s) is an even or odd IP in each case. According to the rules R1, R2 and convention C1-C3, it is found that $$n(s, x, \alpha(\theta_1^-)) = \begin{cases} sgn(\alpha(\theta_1) \cdot \dot{y}(s)), & x \in U_+, \\ -sgn(\alpha(\theta_1) \cdot \dot{y}(s)), & x \in U_-, \end{cases} \tag{10}$$

$$n(s, x, \alpha(\theta_2^+)) = \begin{cases} -sgn(\alpha(\theta_2) \cdot \dot{y}(s)), & x \in U_+, \\ sgn(\alpha(\theta_2) \cdot \dot{y}(s)), & x \in U_-. \end{cases}$$

is obtained. Combining equations 9, 10, and 6 gives $$c_1(s, x) = \begin{cases} -sgn(\alpha(\theta_1) \cdot \dot{y}(s)), & x \in U_+, \\ sgn(\alpha(\theta_1) \cdot \dot{y}(s)), & x \in U_-, \end{cases} \quad c_2(s, x) = -c_1(s, x). \tag{11}$$

Similarly to A. Katsevich, A general scheme for constructing inversion algorithms for cone beam CT, International Journal of Mathematics and Mathematical Science, 21 (2003), pp. 1305-1321 it is seen that when $\Pi_{flt}$ is a filtering plane for one particular x, then all $x' \in \Pi_{flt}$ share $\Pi_{flt}$ as their filtering plane. Thus, the inversion formula given by equations 6 and 7 is of the shift-variant FBP type. Also see the paragraph following equation 16 below, for more details.

From the above discussion it follows that the algorithm is essentially independent of the curve L. For each $y(s) \in L$ the only thing one needs to know is how C projects onto the detector. This projection depends only on the location of the detector and the coordinates of y(s), but does not depend on the global properties of L. This property makes the algorithm especially convenient for circle-plus trajectories, which are implemented using a rotating gantry and moving table. Regardless of how the table moves during the scan, in this case the curve L lies on the surface of the cylinder with base C. The projection of C onto the detector depends only on the axial distance between $y(s) \in L$ and the plane of the circle.

Consequently, the algorithm is completely independent of the shape of L as long as the main condition at the beginning of this section is satisfied. This means, in particular, that the complete circle+line algorithm described in A. Katsevich, A general scheme for constructing inversion algorithms for cone beam CT, International Journal of Mathematics and Mathical Science 21 (2003), pp. 1305-1321 works for many other trajectories, e.g. circle+helix, circle+variable pitch helix, etc., with almost no modifications. Only the derivative along the source trajectory needs to be changed. Another implication is that in all these cases both the detector requirements and the axial extent of the additional scan L are exactly the same as in the circle+line case described in A. Katsevich (2003).

The computational structure of the algorithm is now described. Let $I_L(x)$ denote the set of all $s \in I_L$ such that the projection of x onto DP(s) appears outside the convex hull of the projection of C onto DP(s). In general the detector moves together with the x-ray source, therefore the position of the detector is also a function of s. So we use the notation DP(s) to describe the position of the detector as a function of s.

Let us describe this in more detail. It is clear that $\alpha^\perp(s,x,\theta_m)$ actually depends only on s and $\beta(s,x)$. Therefore, equations 12 and 13 are included:

$$\alpha_m(s,\beta) = \alpha^\perp(s,x,\theta_m), e_m(s,\beta) := \beta \times \alpha_m^\perp(s,\beta), \beta = (s,x), \tag{12}$$

$$\Phi_m(s, \beta) := \int_0^{2\pi} \frac{\partial}{\partial q} D_f(y(q), \cos\gamma\beta + \sin\gamma e_m(s, \beta))\Big|_{q=s} \frac{1}{\sin\gamma} d\gamma, \tag{13}$$

$$f(x) = -\frac{1}{4\pi^2} \sum_m \int_{I_C \cup I_L(x)} \frac{c_m(s, x)}{|x - y(s)|} \Phi_m(s, \beta(s, x)) ds, \tag{14}$$

where m=1, 2, . . . if the source is on C, and m=1, 2 if the source is on L. When the source is on C, the number of m values for each y(s) and x equals to the number of lines which are tangent to the projection of C onto DP(s) and pass through the projection of x onto DP(s) plus one.

In actual computations it is convenient to first compute the function $$\Psi_m(s, \Theta) := \frac{\partial}{\partial q} D_f(y(q), \Theta), \tag{15}$$

and then compute $$\Phi_m(s, \beta) := \int_0^{2\pi} \Psi_m(s, \cos\gamma\beta + \sin\gamma e_m(s, \beta)) \frac{1}{\sin\gamma} d\gamma. \tag{16}$$

Any source position y(s) and a filtering line from the corresponding family (either $L_1$ or $L_2$, depending on whether $y(s) \in C$ or $y(s) \in L$), determine a plane. The plane is referred to as a filtering plane. Since $e(s,\beta) \cdot \beta = 0, |e(s,\beta)| = 1$, using equation 12

$$\beta = (\cos\theta, \sin\theta); \; e_k(s,\beta) = (-\sin\theta, \cos\theta) \tag{17}$$

for all $\beta$, $e_k(s,\beta)$ confined to a filtering plane. Here $\theta$ denotes a polar angle within the filtering plane. Therefore, $$\Phi_m(s, \beta) := \int_0^{2\pi} \Psi_m(s, (\cos(\theta + \gamma), \sin(\theta + \gamma))) \frac{1}{\sin\gamma} d\gamma \tag{18}$$

for all $\beta$ confined to a filtering plane.

Equation 16 is of the convolution type and one application of Fast Fourier Transform (FFT) gives values of $\Phi_m(s,\beta)$ for all $\beta$ confined to the filtering plane at once. Equations 14, 15 and 16 would represent that the resulting algorithm is of the convolution-based FBP type. This means that processing of every CB projection consists of two steps. First, shift-invariant and x-independent filtering along a family of lines on the detector is performed. Second, the result is back-projected to update the image matrix. A property of the back-projection step is that for any point z on the detector the value obtained by filtering at $\hat{x}$ is used for all points x on the line segment connecting the current source position y(s) with $\hat{x}$. Since $\partial/\partial q$ in equation 16 is a local operation, each CB projection is stored in memory as soon as it has been acquired for a short period of time for computing this derivative at a few nearby points and is not used later.

To test the results, two numerical experiments were conducted with the clock phantom, which was originally described in H. Turbell et al, Helical cone beam tomography, Int. Journal of Imaging System and Technology, 11 (2000), pp. 91-100. Version of the phantom according to the present invention is a superposition of a cylinder with radius 240 mm and two sets of spheres. The first set consists of 12 spheres with radius 24 mm placed on a helix of radius 192 mm and pitch 28.8 mm. The second consists of 12 spheres of radius 12 mm placed on a helix in the opposite direction with radius 120 mm and pitch 28.8 mm. The background cylinder is at 0 HU, the spheres are at 1000 HU, and the air at −1000 HU. Additional stimulation and reconstruction parameters are listed in Table 1.

TABLE 1

| Simulation parameters | |
|---|---|
| R (radius of the circle and helix) | 600 mm |
| detector pixel size in each direction (as projected to isocenter) | $0.9 \cdot 10^{-3}$ rad × 0.5 mm |
| number of detector rows | 325 |
| number of detectors per row | 1024 |
| number of source positions per rotation (circle and both helices) | 1000 |
| Reconstruction parameters | |
| number of points per convolution | 2048 |
| voxel size in each direction | 1.0 mm |
| number of filtering lines when y(s) ∈ C | 151 |
| number of filtering lines when y(s) ∈ L | 450 |

In both experiments C is a circle of radius R in the plane $x_3=0$ and centered at the origin. The clock phantom is shifted by $\Delta x_3 = 40$ mm up. This is done to illustrate how the algorithm reconstructs cross-sections away from the plane of the circle. In the first experiment the curve L is a constant-pitch helix $$y_1(s)=R\cos s,\ y_2(s)=R\sin s,\ y_3(s)=(h/2\pi)s, \quad (19)$$

where h=50 mm. In the second experiment L is a variable-pitch helix $$y_1(s)=R\cos s,\ y_2(s)=R\sin s,\ y_3(s)=bs^2 sgn(s), \quad (20)$$

where b=0.4.

Figure 13A:
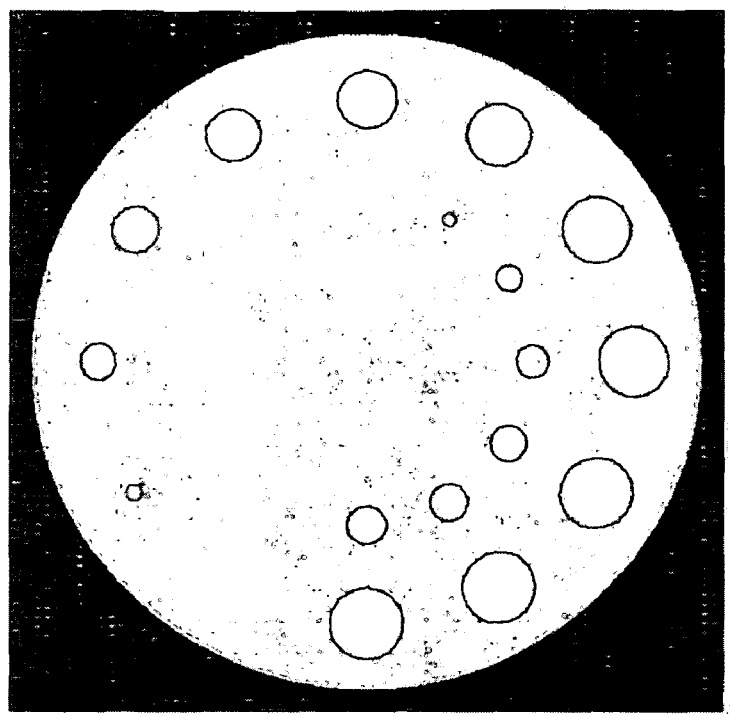
FIG. 13a shows cross-section $x_3$=40 mm through the reconstructed clock phantom for a constant pitch case.
Figure 13B:
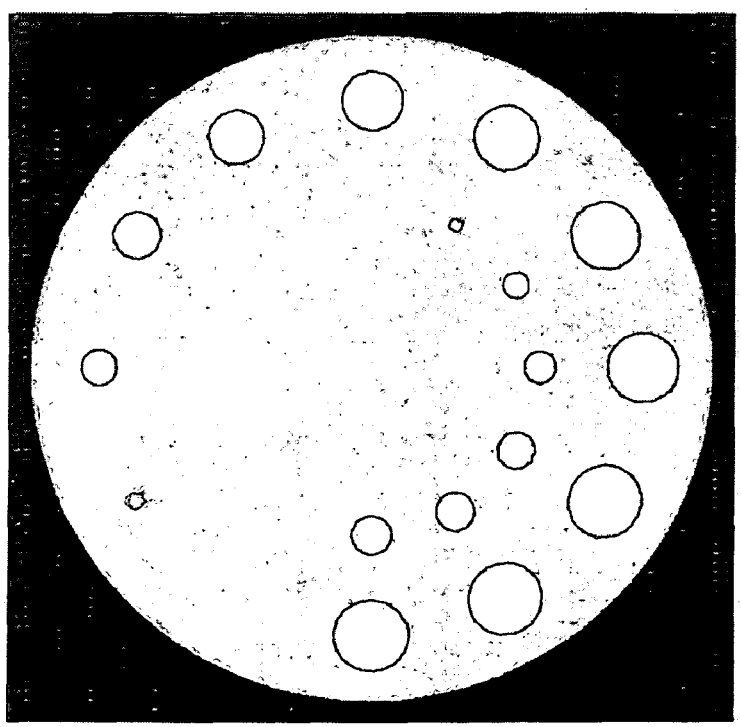
FIG. 13b shows cross-section $x_3$=40 mm through the reconstructed clock phantom for a variable pitch case.

For reconstructions the circle+line algorithm described in A. Katsevich, A general scheme for constructing inversion algorithms for cone beam CT, International Journal of Mathematics and Mathematical Science, 21 (2003), pp. 1305-1321 is used. As previously described, the detector requirements and the axial extent of the helices are the same as in Katsevich (2003). The only difference is that the cylindrical detector geometry is used. According to the theory, the algorithm works without modifications and provide good image quality. The results are shown in FIGS. 13a and 13b. FIG. 13a shows cross-sections $x_3=40$ mm through the reconstructed clock phantom for a constant pitch case. The region $|x_1|, |x_2| \leq 255.5$ is shown. WL=1000 HU. FIG. 13b shows cross-sections $x_3=40$ mm through the reconstructed clock phantom for a variable pitch case. The region $|x_1|, |x_2| \leq 255.5$ is shown. WL=0 HU, WW=100 HU. As shown, the image quality is consistent with a theoretically exact algorithm.

Figure 14A:
FIG. 14a shows cross-section $x_2$=0 mm through the reconstructed disk phantom for a constant pitch case.
Figure 14B:
FIG. 14b shows cross-section $x_2$=0 mm through the reconstructed disk phantom for a variable pitch case.

In the second set of experiments we reconstruct a disk phantom. The phantom is a superposition of a cylinder with radius 240 mm and two sets of identical ellipsoids: lengths of half-axes—40 mm, 40 mm, and 5 mm, distance between centers of neighboring ellipsoids—15 mm. The first set have centers along the line $x_1=-150$ mm, $x_2=0$, and the second set—along the line $x_1=150$ mm, $x_2=0$. The background cylinder is at 0 HU, the ellipsoids are at 1000 HU, and the air is at −1000 HU. All other simulation and reconstruction parameters are the same as in the first set of experiments (cf. Table 1). The results are shown in FIGS. 14a and 14b. FIG. 14a shows the constant pitch case, and the FIG. 14b shows the variable pitch case. Again it is shown that image quality is consistent with a theoretically exact algorithm.

Figure 2:
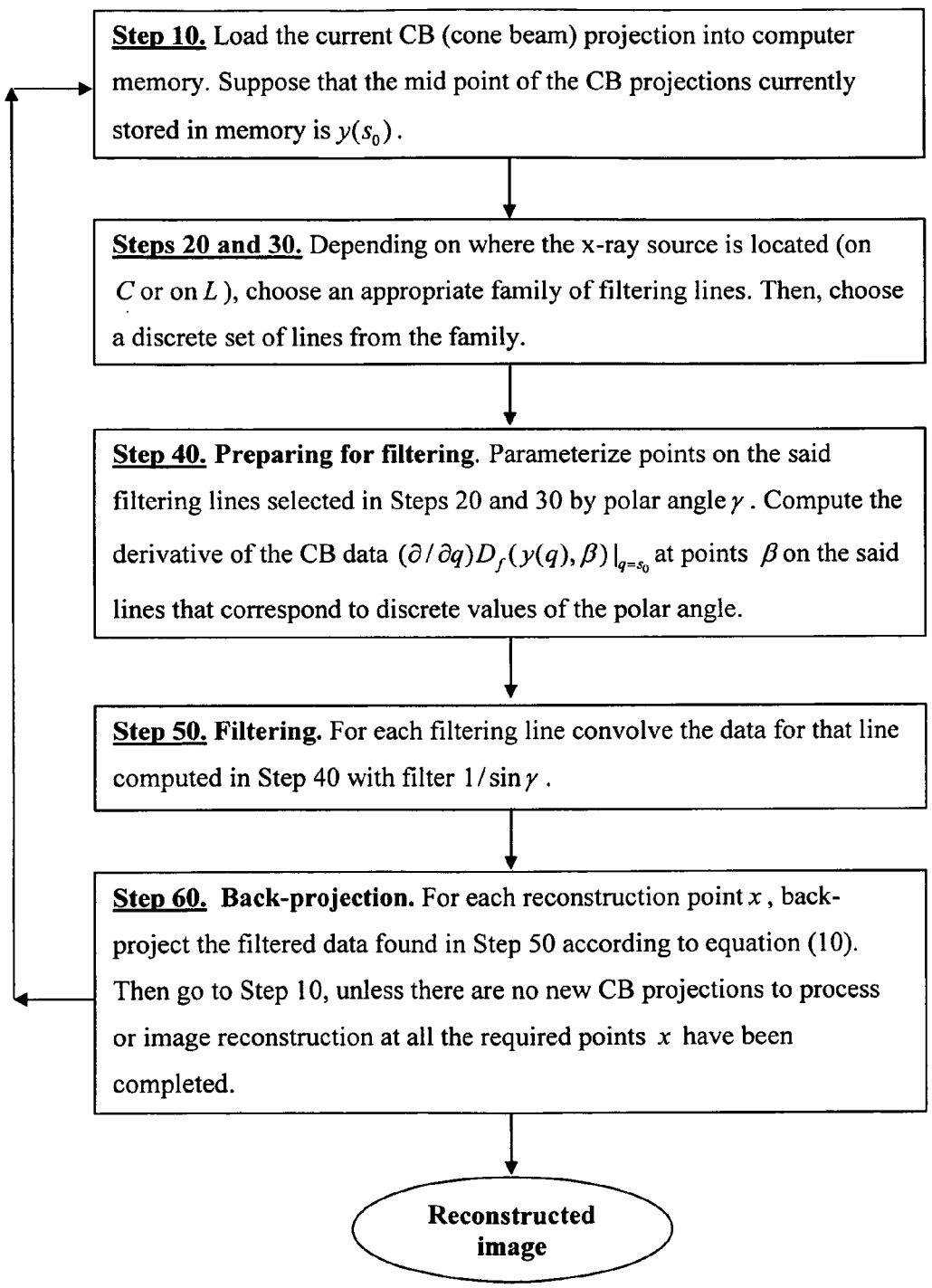
FIG. 2 shows an overview of the basic process steps of the invention that occur during the image reconstruction process.

FIG. 2 is a process flow diagram that shows the six step 10 through 60 for reconstructing an image according to the present invention. In step 10 the current CB (cone beam) projection is loaded into computer memory. Suppose that the midpoint of the CB projections currently stored in memory is $y(s_0)$. The detector plane corresponding to the x-ray source located at $y(s_0)$ is denoted $DP(s_0)$.

In steps 20 and 30, depending on where the x-ray source is located (on C or on L), an appropriate family of filtering lines is selected then, a discrete set of lines from the family is selected. FIG. 8 is a three substep flow chart for identifying the set of lines, which corresponds to step 20 shown in FIG. 2. In this example, it is assumed that the x-ray source is located on C.

Figure 5:
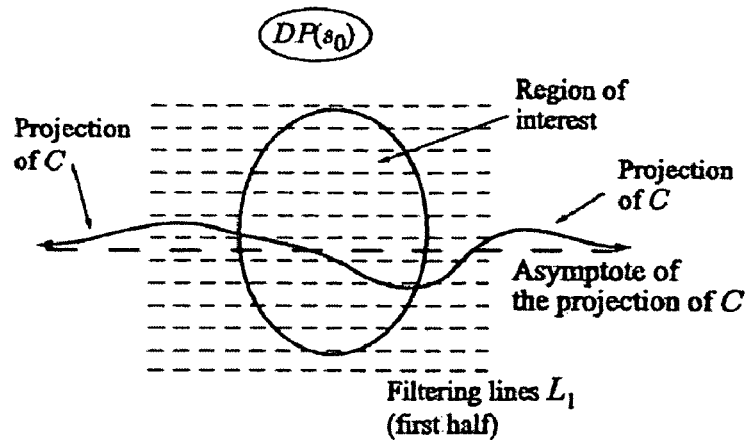
FIG. 5 shows the first half of the family of filtering lines $L_1$.
Figure 6:
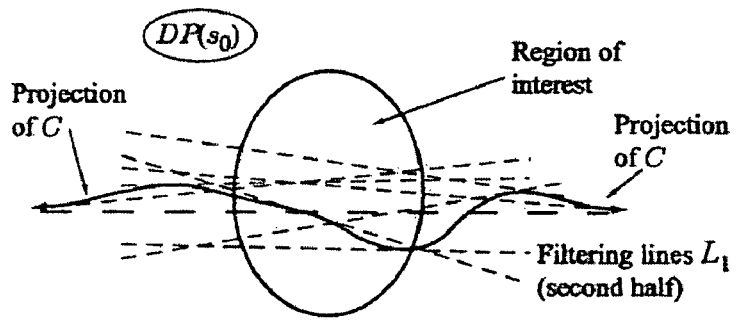
FIG. 6 shows the second half of the family of filtering lines $L_1$.

Referring to FIG. 5 in conjunction with FIG. 8, in step 21 form a set of lines parallel to the asymptote of the projection of C onto the detector that cover the projection of the region of interest inside the object being scanned. These lines are called the first half of the filtering family $L_1$. Referring to FIG. 6 in conjunction with the flow diagram shown in FIG. 8, form a set of lines tangent to the projection of C onto the detector. These lines are called the second half of the filtering family $L_1$ in step 22. In step 23 the two halves obtained in Steps 21 and 22 are combined to form the family of filtering lines $L_1$.

Figure 7:
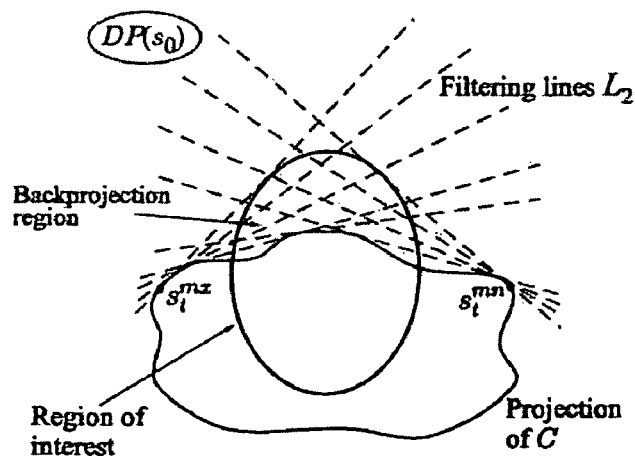
FIG. 7 shows the family of filtering lines $L_2$.

FIG. 9 is a process flow diagram showing the three substeps for identifying the set of lines, which corresponds to step 30 shown in FIG. 2. In step 30 it is assumed that the x-ray source is located on L. Referring to FIG. 7, the set of lines can be selected by the steps 31, 32, and 33. In step 31, a discrete set of values of the parameter $s_t$ inside the interval $[s_t^{min}, s_t^{max}]$ is selected. For each $s_t$ chosen in step 31 find a line tangent to the projection of C is located in step 32. In step 33, from the collection of lines constructed in Step 32 retain only the lines that are tangent to the convex hull of the projection of C. The remaining lines form the required set of lines, which is called family $L_2$. FIG. 7 shows the family of lines used in the algorithm of the invention).

Referring back to FIG. 2, in step 40 the data collected is prepared for filtering. Points on the filtering lines selected in steps 20 and 30 are parameterized by polar angle $\gamma$. The derivatives of the CB data $(\partial/\partial q)D_f(y(q)\beta)|_{q=s_0}$ at points $\beta$ on the said lines that correspond to discrete values of the polar angle are computed. FIG. 10 shows the seven steps for preparation for filtering.

If the x-ray source is located on C, in step 41 a filtering line $l_{ft} \in L_1$ from the set of lines obtained in step 20 is fixed. If the x-ray source is located on L, fix a filtering line $l_{ft} \in L_2$ from the set of lines obtained in Step 30. In step 42 points on the line by polar angle γ in the plane through $y(s_0)$ and $l_{ft}$ are parameterized. In step 43 a discrete set of equidistant values $γ_j$ are chosen for use later for discrete filtering in step 50. For each $γ_j$ the unit vector $β_j$ which points from $y(s_0)$ towards the point on $l_{ft}$ that corresponds to $γ_j$ is found in step 44. In step 45, using the CB projection data $D_f(y(q),Θ)$ for a few values of q close to $s_0$ the derivative $(∂/∂q)D_f(y(q),Θ)|_{q=s_0}$ for all $Θ=β_j$ numerically is found. The computed values of the derivative in computer memory in step 46. In step 47 steps 41-46 are repeated for all lines $l_{ft}$ to create the processed CB data $Ψ(s_0,β_j)$ corresponding to the x-ray source located at $y(s_0)$.

For each filtering line convolve the data for that line computed in Step 40 with filter 1/sin γ in step 50. FIG. 11 is a seven step flow chart for filtering, which corresponds to step 50 of FIG. 2. In step 51 a filtering line $l_{ft}$ is fixed. When the x-ray source is located on L, take $l_{ft} \in L_1$. When the x-ray source is located on the circle C, take $l_{ft} \in L_2$. The TFT (Fast Fourier Transform) of the values of the processed CB data computed in step 40 are computed along the line in step 52.

The FFT of the filter 1/sin γ is computed in step 53 and in step 54 the FFT of the filter 1/sin γ (the result of Steps 53) and FFT of the values of the processed CB data resulting from steps 52 are multiplied. Then the inverse FFT of the result of step 54 is taken in step 55 and the result of step 55 is stored in computer memory in step 56. Steps 51-56 are repeated in step 57 for all lines in the said family of lines. This will give the filtered CB data $Φ(s_0,β_j)$. By itself the filtering step can be well known in the field and can be implemented, for example, as shown and described in U.S. Pat. No. 5,881,123 to Tam, which is incorporated by reference.

Referring to FIG. 2, step 60 is the back-projection step where for each reconstruction point of the filtered data found in step 50 is back-projected according to equation (10). The process returns to step 10 unless there are no new CB projections to process or image reconstruction at all the required points have been completed. FIG. 12 is a flow chart sowing the steps for back projection. A reconstruction point x is fixed in step 61, x represents a point inside the patient where it is required to reconstruct the image. When $s_0$ belongs to $I_C \cup I_L(x)$ in step 62, then the filtered CB data affects the image at x and one performs steps 63-68. When $s_0$ is not inside $I_C \cup I_L(x)$, then the filtered CB data is not used for image reconstruction at x and the process returns to step 61 to select another reconstruction point.

In step 63 the projection $\hat{x}$ of x onto the detector plane $DP(s_0)$ and the unit vector $β(s_0,x)$ are found, which points from $y(s_0)$ towards x. The filtering lines $l_{ft} \in L_1$ or $l_{ft} \in L_2$ (depending on where the x-ray source is located) and points on the said lines that are close to the said projection $\hat{x}$ are identified in step 64. This gives a few values of $Φ_m(s_0, β_j)$, m=1, 2, ..., for $β_j$ close to $β(s_0,x)$. Using interpolation in step 65, the value of $Φ_m(s_0,β(s_0,x))$ from the values of $Φ_m(s_0,β_j)$ for $β_j$ close to $β(s_0,x)$ for each m=1, 2, ... is estimated.

The contribution from the said filtered CB data to the image being reconstructed at the point x is computed in step 66 by multiplying $Φ_m(s_0,β(s_0,x))$ by $-c_m(s_0,x)/(4π^2|x-y(s_0)|)$. The quantity $c_m(s_0,x)$ is defined by equation 6. In step 67, add the contribution to the image being reconstructed at the point x according to a pre-selected scheme (for example, the Trapezoidal scheme) for approximate evaluation of the integral in equation 14. The back projection process is repeated in step 68 by returning to step 61 and selecting a different reconstruction point x.

In the final step, step 70, The process is repeated by going back to step 10 shown in FIG. 2 and loading the next CB projection into computer memory. The image can be displayed at all reconstruction points x for which the image reconstruction process has been completed (that is, all the subsequent CB projections are not needed for reconstructing the image at those points). Discard from the computer memory all the CB projections that are not needed for image reconstruction at points where the image reconstruction process has not completed. The process concludes when the scan is finished or the image reconstruction process has completed at all the required points.

The invention is not limited to an object that undergoes a scan consisting of a single closed curve C and a single additional curve L. The algorithm can be applied to trajectories consisting of several closed curves and additional non-closed curves by applying it to various C+L pairs, and then combining the results. The algorithm can be changed by modifying the filtering step to improve efficiency and resolution, but keeping the overall structure the same, thereby obtaining quasi-exact reconstruction. The required CB data need not be obtained directly from a C+L scan, but rather collected from a different type of scan and then extracted or synthesized using, e.g., interpolation.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method for reconstructing an exact or quasi-exact image from cone beam data provided by at least one detector for a general circle-plus trajectory comprising the steps of:
   (a) scanning an object using an x-ray source;
   (b) collecting cone beam data of the object, wherein the cone beam data corresponds to a general circle-plus trajectory relative to the object; the general circle-plus trajectory including a C component and an L component, wherein C is any closed continuous curve, and L is an additional curve that starts on or below C and ends above C that guarantees completeness of the cone beam data for at least one reconstruction point regardless of movement of the x-ray source during the scanning step; and
   (c) reconstructing an exact or quasi-exact image of the scanned object from the circle-plus trajectory cone beam data using a convolution based Filtered Back Projection algorithm, wherein for each point on L the step of reconstructing does not depend on the global properties of L.

2. The method of claim 1 wherein component L is a constant pitch helix.

3. The method of claim 1, wherein component L is a variable pitch helix.

4. The method of claim 1, wherein the C component is a circle, and component L lies on a surface of a cylinder with base C as the component C.

5. The method of claim 1, wherein the step of reconstructing further includes the steps of:
   shift invariant filtering of the cone beam data; and
   back projection updating the exact or quasi-exact image of the scanned object.

6. The method of claim 5, wherein for each source position on the component L the step of shift invariant filtering is independent of global properties of L, and a direction of filtering is determined by how the component C projects on the detector.

7. The method of claim 5, wherein for each source position on the component L the step of back projection updating is independent of the global properties of L.

8. The method of claim 6, wherein for each source position on the component L filtering is performed along curves tangent to a convex hull of the projection of component C on the detector.

9. The method of claim 1, wherein the step of reconstructing includes the steps of:
  storing approximately 2 to approximately 4 cone beam projections in memory at a time; and
  using one family of lines for the step of reconstructing when the source is on the component L.

10. The method of claim 1, wherein the step of reconstructing includes the steps of:
  storing one single cone beam projection in memory at a time; and
  using one family of lines for the step of reconstructing when the source is on the component L.

11. The method of claim 1 further comprising the step of:
  identifying lines on a plane Π intersecting the cone beam, the identification including the steps of:
  when the x-ray source belongs to the component C, project C onto Π and select a discrete set of lines tangent to that projection or parallel to an asymptote of the projection; and
  when the x-ray source belongs to the component L, project C onto Π and select a discrete set of lines tangent to a convex hull of that projection.

12. A method for reconstructing an image from cone beam data provided by at least one detector for a general circle-plus trajectory comprising the steps of:
  (a) scanning an object using an x-ray source;
  (b) collecting cone beam data of the object, wherein the cone beam data corresponds to a general circle-plus trajectory relative to the object; the general circle-plus trajectory including a C component and an L component, wherein C is any closed curve, and L is an additional curve;
  (c) identifying lines on a plane Π intersecting the cone beam, the identification including the steps of:
    (ci) when the x-ray source belongs to the component C, project C onto Π and select a discrete set of lines tangent to that projection or parallel to an asymptote of the projection; and
    (cii) when the x-ray source belongs to the component L, project C onto Π and select a discrete set of lines tangent to a convex hull of that projection;
  (d) preprocessing and shift invariant filtering said data along said lines;
  (e) back projecting said filtered data to form a precursor of said image; and
  (f) repeating steps a, b, c, d, and e until the image of the object is reconstructed.

13. The method of claim 12, wherein the step (d) of preprocessing includes computing a derivative $(\partial/\partial s)D_f(y(s),\Theta)$, wherein s is a parameter along a scan path, which determines point $y(s)$ on the path, $D_f(y,\Theta)$ is a cone beam transform of $f$ corresponding to the x-ray source located at a point y and a direction $\Theta$, and $f$ is a function describing the object being scanned.

14. The method of claim 12, further comprising the steps of:
  storing approximately 2 to approximately 4 cone beam projections in memory at a time; and
  using one family of lines for each x-ray source position for the step of filtering when the source is on L.

15. The method of claim 12, wherein the back projection step (e) includes the steps of:
  (ei) fixing a reconstruction point x which represents a point inside the object being scanned to reconstruct the image;
  (eii) fixing a source position $y(s)$ on L and locating a projection $\hat{x}$ of x onto the detector which corresponds to the source located at source position $y(s)$;
  (eiii) when $\hat{x}$ is projected inside a convex hull of the projection of component C on the detector, the cone beam data corresponding to source position $y(s)$ is not used for image reconstruction at x; and
  (eix) when $\hat{x}$ is projected outside the convex hull of the projection of C on the detector, the cone beam data corresponding to source position $y(s)$ is used for image reconstruction at x.

16. A method for reconstructing an exact or quasi-exact image from cone beam data provided by at least one detector for a circle-plus trajectory comprising the steps of
  (a) scanning an object using an x-ray source,
  (b) collecting cone beam data of the object, wherein the cone beam data corresponds to a circle-plus trajectory relative to the object, the circle-plus trajectory including a C component and an L component, wherein component C is a circle, and component L is an additional curve that starts on or below C and ends above C and which lies on the surface of a right circular cylinder with base C; and
  (c) reconstructing an exact or quasi-exact image of the scanned object from the circle-plus trajectory cone beam data using a convolution based Filtered Back Projection algorithm, wherein for each source position on component L, the source being physical or virtual, the step of reconstructing depends only on a distance between a current source position and a plane of component C and on the properties of component L in a neighborhood of the current source position.

17. The method of claim 16, wherein component L is a constant pitch helix.

18. The method of claim 16, wherein component L is a variable pitch helix.

19. The method of claim 16, wherein the step of reconstructing further includes the steps of:
  shift invariant filtering of the cone beam data projections; and
  back projection updating the image of the scanned object.

20. The method of claim 19, wherein for each source position on the component L filtering is performed along curves tangent to the projection of component C on the detector.

* * * * *